US00PP28027P2

(12) United States Plant Patent
Sato et al.

(10) Patent No.: US PP28,027 P2
(45) Date of Patent: May 16, 2017

(54) **NEW GUINEA *IMPATIENS* PLANT NAMED 'SAKIMP037'**

(50) Latin Name: ***Impatiens hybrida* hort**
Varietal Denomination: SAKIMP037

(71) Applicant: Sakata Seed Corporation, Yokohama (JP)

(72) Inventors: Chihiro Sato, Nagano (JP); Shinji Minemura, Nagano (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 14/999,129

(22) Filed: Mar. 31, 2016

(51) Int. Cl.
*A01H 5/02* (2006.01)

(52) U.S. Cl.
USPC ..... Plt./318.5

(58) Field of Classification Search
USPC ..... Plt./318.5, 318.4, 318.6
CPC ..... A01H 5/0261
See application file for complete search history.

*Primary Examiner* — Kent L Bell
(74) *Attorney, Agent, or Firm* — Barbara Campbell; Bethany R. Roahrig; Cochran Freund & Young, LLC

(57) ABSTRACT

An *impatiens* plant particularly distinguished by having pink flowers, and green leaves with yellow variegation, is disclosed.

2 Drawing Sheets

Genus and species: *Impatiens hybrida* hort.
Variety denomination: 'SAKIMP037'.

BACKGROUND OF THE NEW PLANT

The present invention comprises of a new and distinct cultivar of New Guinea *Impatiens*, botanically known as *Impatiens hybrida* hort, and referred to by the variety name 'SAKIMP037'. 'SAKIMP037' originated from an interspecific hybridization between *Impatiens* 'NE-4391', an unpatented proprietary white flowered *Impatiens* breeding line and *Impatiens* 'NF-4858', an unpatented proprietary scarlet flowered *Impatiens* breeding line in Misato, Japan.

In September 2009, the female parent line 'NE-4391' and male parent line 'NF-4858' were crossed and a population of $F_1$ plants was created. The $F_1$ plants were evaluated in Misato, Japan in an open field trial. The criteria for plant selection included compact growth habit, vigorous rooting, bright flower color and variegated leaves. At the completion of the trial, one single-plant selection was made based on the above criteria and vegetatively propagated. From June to August 2012, the selection was evaluated in an open field in Misato, Japan. Shoot-tip cuttings of the variety were then shipped to Salinas, Calif., where the plants were regenerated and reevaluated for stability of traits. The selection subsequently was named 'SAKIMP037' and found to have its unique characteristics reproduce true to type in successive generations of asexual propagation via vegetative cuttings in Salinas, Calif.

SUMMARY

The following are the most outstanding and distinguishing characteristics of this new variety when grown under normal horticultural practices in Salinas, Calif.

1. Pink flowers; and
2. Green leaves with yellow variegation.

CROSS-REFERENCE TO RELATED APPLICATIONS

An application for plant breeders rights was filed with the Japan Plant Variety Protection Office on Sep. 28, 2015, Application No. 30479. 'SAKIMP037' has not been made publicly available more than one year prior to the filing date of the instant application.

DESCRIPTION OF THE PHOTOGRAPHS

This impatiens plant is illustrated by the accompanying photographs which show the plant's overall plant habit including form, foliage, and flowers. The photographs are of a plant grown in Salinas, Calif. under greenhouse conditions. The colors shown are as true as can be reasonably obtained by conventional photographic procedures.

DESCRIPTION OF THE NEW VARIETY

Figure 1:
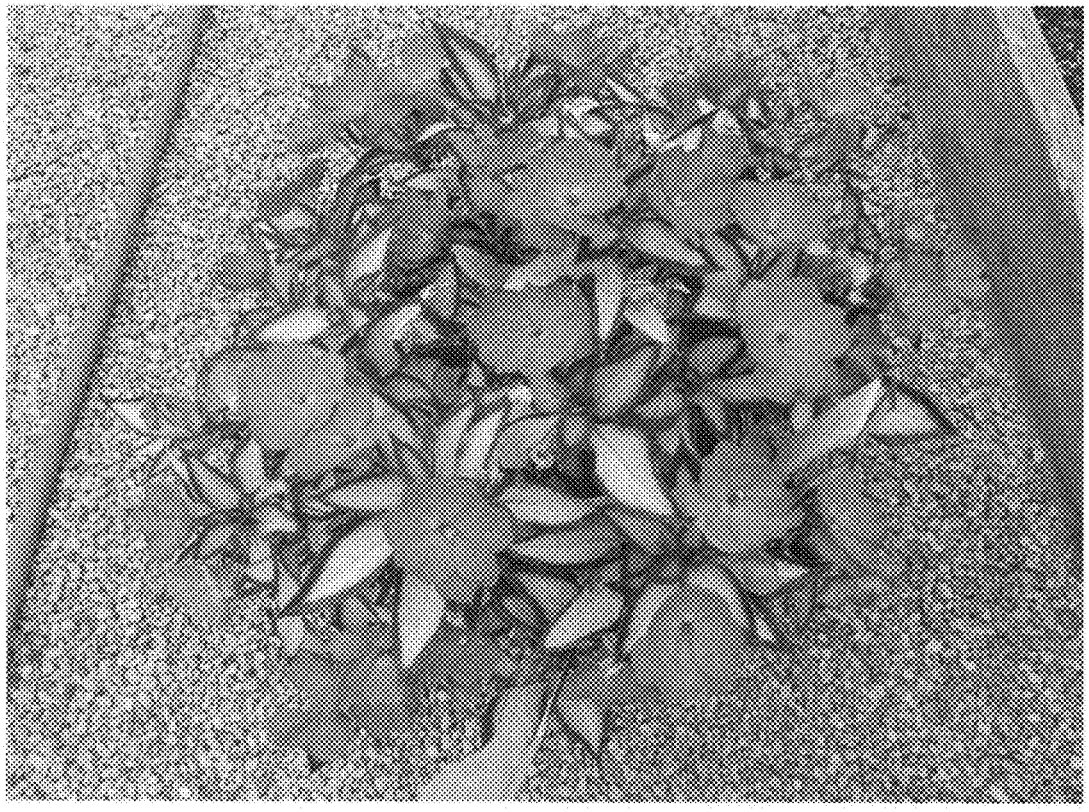
FIG. 1 shows the overall plant habit of the plant grown in a pot.
Figure 2:
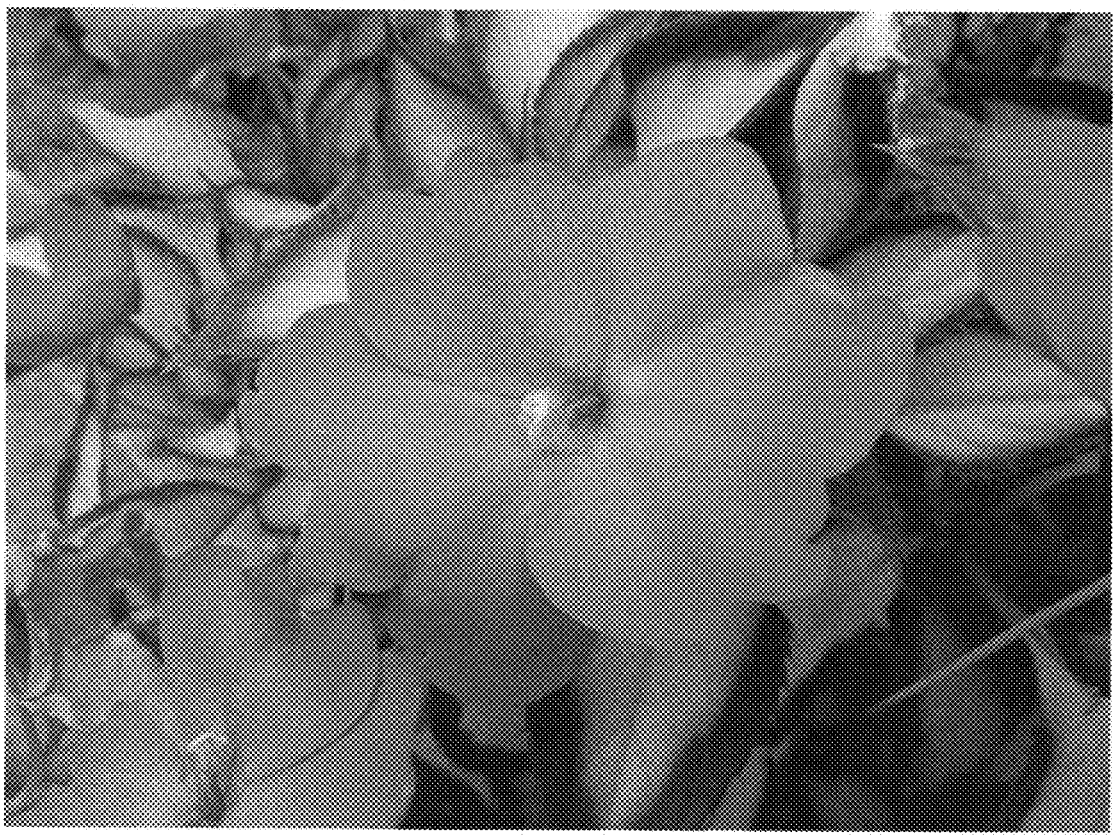
FIG. 2 shows a close-up of the mature inflorescence of the plant.

The following detailed descriptions set forth the distinctive characteristics of 'SAKIMP037'. Data was collected on plants grown about 4 months from propagation by terminal cutting in Salinas, Calif., under greenhouse conditions, in Salinas, Calif. Color references are to The Royal Horticultural Society of London color chart (R.H.S.), $4^{th}$ edition (2001). Anatomic labels are from *The Cambridge Illustrated Glossary of Botanical Terms*, by M. Hickey and C. King, Cambridge University Press.

Classification and parentage:

*Family*.—Balsaminaceae.
*Botanical*.—*Impatiens hybrida* hort.
*Common*.—*Impatiens*.

*Designation*.—'SAKIMP037'.

*Parentage*.—Female Parent: Proprietary *Impatiens* plant line 'NE-4391'. Male Parent: Proprietary *Impatiens* plant line 'NF-4858'.

Growth:

*Environmental conditions for plant growth*.—The terminal 1.0 to 1.5 inches of an actively growing stem was excised. The vegetative cuttings were propagated for five to six weeks. The base of the cuttings were dipped for 1 to 2 seconds in a 1:9 solution of DIP 'N GROW (1 solution: 9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed. Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24° C.

Plant description:

*Life cycle*.—Annual.

*Flowering requirements* (*season*).—Spring to first frost.

*Temperature tolerances*.—Heat tolerant, plants observed to continue flowering in a temperature range of 5° C. to 36° C.

*Habit*.—Compact.

*Height*.—24.0 cm from soil line to top of foliage.

*Spread*.—40.0 cm.

*Number of branches*.—14 total with 4 main branches.

*Length of branches*.—1.5 cm from soil line to first node, 10.0 cm total.

*Diameter of branches*.—2.0 cm for the main branch.

*Color of branches*.—RHS 59A (Red-Purple).

*Time to produce a rooted cutting*.—About 4 weeks.

*Time to bloom from propagation*.—6 to 8 weeks.

Stems/branches:

*Stem description*.—Smooth; circular cross-section, strong and shiny.

*Stem color*.—RHS 59B (Red-Purple).

*Anthocyanin color*.—RHS 59B (Red-Purple).

*Stem pubescence*.—Absent.

*Stem length*.—5.0 cm to 7.0 cm from first to second node, 9.0 cm to 10.0 cm total.

*Stem diameter*.—7.0 cm.

*Internode length*.—5.0 cm to 7.0 cm.

Leaves:

*Leaf arrangement*.—Whorled with up to 5 leaves per node, opposite if only two leaves at one node.

*Shape*.—Lanceolate; curled.

*Apex*.—Acuminate.

*Base*.—Shortly attenuate.

*Margin*.—Serrate.

*Surface*.—Dull, waxy.

*Length*.—7.0 cm to 10.0 cm.

*Width*.—3.0 cm 4.0 cm.

*Color*.—Upper surface: RHS 139A (Green) around outer edge with RHS 11B (Yellow) from inside edge to center. Lower surface: RHS 189A (Greyed-Green) around outer edge with RHS 11C (Yellow) from inside edge to center.

*Variegation*.—Present; length of yellow area is 7.5 cm to 9.0 cm; diameter of yellow area is 3.0 cm to 3.5 cm; diameter of green area is 0.2 cm to 0.5 cm around outer edge.

*Fragrance*.—Absent.

*Pubescence*.—Absent.

*Petiole*.—Length: 2.0 cm to 3.0 cm. Diameter: 0.3 cm to 0.4 cm. Color: RHS 59D (Red-Purple). Texture: Smooth, glabrous. Venation: Pinnate.

*Venation color*.—Upper surface: RHS 155C (White) to the edge, then RHS 139A (Green) at the edge. Lower surface: RHS N155D (White) to the edge, then RHS 189A (Greyed-Green) at the edge.

Inflorescence:

*Inflorescence type*.—Single flowers with spur; 5 petals.

*Fragrance*.—Absent.

*Number of flowers per node*.—1 to 3 in bloom at one time; about 10 flower buds.

*Number of flowers per plant*.—25 to 30 in bloom.

*Lastingness of individual blooms on the plant*.—14 days.

Corolla:

*Shape*.—Roughly circular with 5 radial petals.

*Diameter*.—About 4.5 cm to 5.0 cm.

*Depth*.—0.5 cm to 1.0 cm.

Calyx:

*Sepal*.—Shape: Lanceolate, curled. Number: 2. Color: RHS 62D (Red-Purple). Length: 0.8 cm to 1.0 cm. Diameter: 0.4 cm to 0.5 cm. Base: Subcordate. Apex: Caudate. Margin: Entire. Texture: Glabrous.

Bud:

*Surface texture and appearance*.—Smooth, shiny, glabrous.

*Shape*.—Deltoid, longitudinal cross-section.

*Length*.—1.5 cm to 1.7 cm.

*Diameter*.—1.0 cm.

*Color*.—RHS 52 B (Red) with RHS 141D (Green) at the edge.

Petals:

*Pubescence*.—Glabrous.

*Length*.—2.5 cm.

*Width*.—2.5 cm.

*Shape*.—Obcordate.

*Apex*.—Emarginate (cleaved).

*Base*.—Attenuate.

*Margin*.—Entire.

*Color*.—Upper surface: RHS 67A (Red-Purple). Lower surface: RHS 67B (Red-Purple). Eye zone: RHS 67C (Red-Purple).

Spur:

*Shape*.—Tubular, curved downward.

*Color*.—RHS 67D (Red-Purple).

*Length*.—3.8 cm 4.0 cm.

*Diameter*.—1.0 mm to 2.0 mm.

Peduncle:

*Peduncle length*.—3.0 cm.

*Color*.—RHS 67C (Red-Purple).

*Diameter*.—1.0 mm to 1.5 mm.

*Texture*.—Smooth, glabrous.

Reproductive organs:

*Stamens*.—Stamen form: Fused; split into 4 lobes. Stamen number: Many. Filament length: 3.0 mm. Filament color: RHS 69B (Red-Purple). Anther length: 4.0 mm. Anther color: N155A (White). Pollen amount: Abundant. Pollen color: RHS 155A (White). Pollen description: Powdery.

*Pistil*.—Pistil number: 5. Stigma color: RHS 143B (Green). Style color: RHS 143B (Green). Ovary arrangement: Parietal. Ovary surface color: RHS 1D (Green-Yellow).

Disease and insect resistance: No particular resistance or susceptibility observed.

Seed production: Absent.

COMPARISON WITH PARENTAL LINES AND COMMERCIAL VARIETY

'SAKIMP037' is distinguished from its parental lines as shown in Table 1 below.

TABLE 1

Comparison with Parental Lines

| Characteristic | 'SAKIMP037' | Male Parent 'NF-4858' | Female Parent 'NE-4391' |
|---|---|---|---|
| Flower color | Pink | Scarlet | White |
| Plant growth habit | Compact | Mounding | Mounding |

'SAKIMP037' is a new and distinct cultivar of *Impatiens* owning to its compact growth habit, bright flower color, variegated leaves and strong root system. 'SAKIMP037' is most similar to the commercial Impatiens variety, 'SAKIMP005', also commercially known as SUNPATIENS 'Spreading Salmon' (U.S. Plant Pat. No. 19,500); however, there are differences as listed in the table below:

TABLE 2

Comparison with Commercial Variety

| Characteristic | 'SAKIMP037' | 'SAKIMP005' |
|---|---|---|
| Growth habit | Compact | Spreading |
| Petal color, upper surface | RHS 67A (Red-Purple) | RHS 52B (Red) |
| Spur color | RHS 67D (Red-Purple) | RHS 52C (Red) |
| Mature leaf color, upper surface | Variegated with RHS 139A (Green) on outer edge and RHS 11B (Yellow) inside edge to center of leaf; leaves of 'SAKIMP037' having more RHS 11B (Yellow) and less RHS 139A than leaves of 'SAKIMP005' | Variegated with RHS 139A (Green) on outer edge and RHS 11B (Yellow) inside edge to center of leaf |

We claim:

1. A new and distinct variety of New Guinea *impatiens* plant named 'SAKIMP037' as described and illustrated herein.

* * * * *